United States Patent [19]

Graebner et al.

[11] Patent Number: 5,620,253

[45] Date of Patent: Apr. 15, 1997

[54] METHOD OF DETERMINING THE THERMAL RESISTIVITY OF ELECTRICALLY INSULATING CRYSTALLINE MATERIALS

[75] Inventors: John E. Graebner, Short Hills; Sungho Jin, Millington, both of N.J.

[73] Assignee: Lucent Technologies Inc., Murray Hill, N.J.

[21] Appl. No.: 509,678

[22] Filed: Jul. 31, 1995

[51] Int. Cl.$^6$ ................................................ G01N 25/20
[52] U.S. Cl. ............................... 374/43; 374/44; 364/556
[58] Field of Search .......................... 374/43, 44; 364/556

[56] References Cited

U.S. PATENT DOCUMENTS

| | | | |
|---|---|---|---|
| 3,552,185 | 1/1971 | Goode, Jr. et al. | 374/44 |
| 3,611,786 | 10/1971 | Schorr | 374/44 |
| 4,372,691 | 2/1983 | Buckley | 374/44 |
| 4,522,512 | 6/1985 | Atkins | 374/44 |
| 5,297,868 | 3/1994 | Graebner | 374/44 |
| 5,302,022 | 4/1994 | Huang et al. | 374/43 |

FOREIGN PATENT DOCUMENTS

| | | | |
|---|---|---|---|
| 2592490 | 7/1987 | France | 374/43 |
| 161649 | 12/1981 | Japan | 374/43 |

OTHER PUBLICATIONS

E. A. Burgemeister, "Thermal Conductivity of Natural Diamond Between 320 and 450 K," *Physica* 93B (1978) pp. 165–179. Comment: As shown in FIG. 1 and accompanying text of this reference, the thermal conductivity of diamond was first measured by means of traditional heat–flow techniques pp. 166–167, especially equation 1). In addition the thermal conductivity of diamond was also measured by means of an infrared absorption technique, but using essentially only one single infrared wavelength at a time, i.e., and extremely narrow spectral range (p. 169, col. 2; p. 173, legend beneath FIG. 5). By contrast, the present invention recognizes that a much wider spectral range can and should be used, which takes the technique out of the laboratory and into the commercial world since the invention does not require spectrometer devices as does the prior art.

D. T. Morelli et al., "Correlating Optical Absorption and Thermal Conductivity in Diamond," *Appl. Phys. Lett.* vol. 63, No. 2, Jul. 12, 1993, pp. 165–167. Comment: This reference also teaches use of only narrow spectral ranges for each absorption measurement (FIG. 1 on p. 166). Likewise, this reference's statement regarding the relationships shown in FIG. 4 is limited to but a single wavelength at a time. There is thus no teaching here of the utility of the much wider spectral ranges taught by the present invention.

*Elementary Physics: Classical and Modern*, by Richard T. Weidner and Robert L. Sells, pp. 306–307 (1975). Comment: This reference is cited on p. 1 of applicant' specification.

*Optics Guide 5*, published by Melles Griot, Irvine, CA 92714, at pp. 22–29 through 22–38 (1990). Comment: This reference is cited on p. 9 of applicants' specification.

*Primary Examiner*—Diego F. F. Gutierrez
*Attorney, Agent, or Firm*—David I. Caplan; Eugen E. Pacher

[57] ABSTRACT

The thermal resistivities $W_s(=1/\kappa_s)$ of electrically insulating, crystalline or polycrystalline samples under test (SUTs), all comprising host material such as CVD diamond, can be determined rather quickly once the thermal resistivities $W=1/\kappa$ of at least two other host crystalline or polycrystalline bodies $B_1$ and $B_2$ comprising the same host material as that of the SUTs, and containing the same type of impurity or combination of impurities as the SUTs, are measured by some other technique. These determinations of these thermal resistivities $W_s$ of the SUTs thus require only the measurements of the optical absorptivities $\alpha_1$ and $\alpha_2$ and of the thermal resistivities $W_1$ and $W_2$, respectively, of at least each of the two other bodies $B_1$ and $B_2$ and only of the optical absorptivities $\alpha_s$ of each of the SUTs by such other technique. These determinations of $W_s$ rely on our discovery that the following linear relationship exists: $W=A+C\alpha$, where A and C are constants so long as the type of impurity or combination of impurities in all the bodies $B_1$, $B_2$, and SUTs is the same, even though the impurities or combination of impurities have different concentrations in the bodies $B_1$ and $B_2$, as well as in the SUTs.

18 Claims, 1 Drawing Sheet

METHOD OF DETERMINING THE THERMAL RESISTIVITY OF ELECTRICALLY INSULATING CRYSTALLINE MATERIALS

FIELD OF THE INVENTION

This invention relates to methods of determining the thermal resistivity and conductivity of crystalline materials, and more particularly, of determining the thermal resistivity and conductivity of electrically insulating materials such as the thermal resistivity and conductivity of artificial and natural crystalline and polycrystalline materials like CVD diamond.

BACKGROUND OF THE INVENTION

In the case of one-dimensional steady-state heat flow through a sample body, its thermal conductivity $\kappa$ is given by $$\kappa = P/[A(\Delta T/\Delta x)] \tag{1}$$

where P is the heat flowing per unit time along the x axis through a cross section of the body, the cross section being oriented parallel to the yz plane and having an area equal to A, and where $\Delta T$ is the temperature drop along a distance $\Delta x$ measured along the x axis as can be measured by attaching to the body a pair of localized temperature sensors (thermometers), typically thermocouple junction (thermocouples), that are spaced apart in the x direction by the distance $\Delta x$. A direct measurement technique that implements this one-dimensional heat flow is generally described in the textbook *Elementary Physics; Classical and Modern*, by Richard T. Weidner and Robert L. Sells, at pages 306–307 (1975).

In that technique, a sample body in the form of a solid circular cylinder ("rod"), having a uniform cross section A and having a pair of end surfaces, is surrounded by an insulating material, in order to minimize heat exchange into or out of the sample body through its side surfaces. One end surface of the body is maintained at a constant high temperature $T_h$, as by means of a hot reservoir or heat source, while the other end surface is maintained at a constant lower temperature $T_c$, as by means of a cold reservoir or heat sink. In the steady state, the heat crossing any cross section of the cylinder per unit time is equal to the same value P given by equation (1) above, and the temperature gradient $\Delta T/\Delta x$ is the same everywhere along the rod, i.e., is independent of the x coordinate.

In prior art, implementation of this sort of one-dimensional technique has been cumbersome and time-consuming, stemming from the need for attaching the heat reservoirs and the thermometers to the sample body each time a different one is to be measured. Also, relatively lengthy and careful measurements are required to account for, and correct for, heat losses. More specifically, the required thermal insulation tends to get in the way of the thermometers (thermocouple junctions) and their wiring, as well as in the way of the heat source and its wiring-the wiring, being fine (small diameter) and fragile, and having a tendency to develop kinks and to be crunched by the required thermal insulating material.

Relevant to solving these problems is U.S. Pat. No. 5,297,868 entitled "Measuring Thermal Conductivity and Apparatus Therefor" issued on Mar. 29, 1994. On the other hand, in some, if not many or most, cases it would be desirable to have available an even taster method for measuring thermal conductivity.

SUMMARY OF THE INVENTION

This invention is based on our discovery that in the case of a wide variety of electrically insulating crystalline or polycrystalline host materials that contain an impurity or a combination of impurities, and in particular the case of chemical vapor deposited (hereinafter: CVD) diamond as host material, the thermal resistivity, $W=1/\kappa$ by definition, satisfies the equation $$W = A + C\alpha \tag{2}$$

where $\alpha$ is the optical absorptivity of the individual bodies, and where C and A are constants, respectively, for all such bodies (polished or unpolished) formed by a given type of host material that contains a given type of impurity or a combination of given types of impurities in a given ratio in that material.

The optical absorptivity $\alpha$ ideally is defined by the equation $I = I_0 \exp(-\alpha t)$, but it is typically measured in practical cases according to the equation $$\alpha = \beta I_0 \exp(-\alpha t) \tag{3}$$

where $\beta$ is a well known (correction) factor involving external surface reflections and multiple internal reflections (caused by the refractive index), where t is the thickness of the body parallel to the propagation direction of the optical radiation, where $I_0$ is the intensity of optical radiation of wavelength $\lambda$, incident on the body, and where I is the intensity of optical radiation of the same wavelength $\lambda$, emerging from the body. For example, in the case of CVD diamond, the factor $\beta$ is equal to 0.71, approximately.

As stated above, equation 2 is valid for all bodies of a host material having a combination of impurities in which the ratios of concentrations among the same impurities are all equal in all the bodies—for example, all bodies of naturally occurring, gem quality diamond containing the impurities boron and nitrogen in a ratio of 3/2 by weight, regardless of the total amount of the impurities (within reasonable limits) in each of the bodies.

In using the above equation (2), especially in practical cases, it is not necessary or desirable that the wavelength $\lambda$, be monochromatic or even nearly monochromatic. Instead $\lambda$, can encompass a wide range of the optical spectrum such as substantially the entire humanly visible range of the spectrum (approximately 400 nm–800 nm) or any range anywhere within the visible that preferably comprises wavelengths having significant intensities continuously spanning a range of spectral width approximately equal to at least 200 nm, so that ordinary sunshine or ordinary ambient artificial visible light can be used. As used here, the term "significant intensity" refers to an intensity that contributes to a measurement of the optical absorption $\alpha$ of a body. Alternatively, a convenient spectral range of wavelengths in the infrared region (e.g., the approximate range of 800 nm–2,000 nm or 800 nm–10,000 nm) of the optical spectrum, preferably having wavelengths of significant intensities continuously spanning a range of spectral width equal to approximately at least 200 nm can be used, either alone or simultaneously advantageously combined with a convenient range in the visible range of the spectrum having wavelengths of significant intensities continuously spanning a range of spectral width approximately equal to at least 200 nm. Moreover, instead of—or preferably in addition to substantially the entire humanly visible range of the spectrum (approximately 400 nm–800 nm) or any range anywhere within the visible that preferably comprises wavelengths having significant intensities continuously spanning a range of spectral width approximately equal to at least 200 nm—a spectral range encompassing approximately 10 nm–10,000 nm can be used preferably having wavelengths of significant intensities continuously spanning a range of spectral width equal to approximately at least 200 nm.

Thus in cases where a given sample-body under test (hereinafter: "given sample" or "SUT") is known to have the same host material and the same type of impurity as two other bodies, the thermal resistivities $W_1=1/\kappa_1$ and $W_2=1/\kappa_2$ (with $W_1 \neq W_2$) of the two other bodies can be measured using, for example, the apparatus and method described in the aforementioned U.S. Pat. No. 5,297,868, thereby yielding the constants A and C of equation (2) above by means of known mathematical techniques advantageously involving best curve-fitting of linear equations. Thus the value of the thermal resistivity $W_s$ of the given sample (SUT) can then be determined simply by measuring the optical absorptivity $\alpha$ of the SUT and determining the thermal resistivity W of the SLIT from equation (2) above.

The thermal resistivities W for the first and second bodies and hence the thermal resistivity $W_s$ for the SUT can be thus measured in a direction either parallel or perpendicular to the plane of (i.e., either parallel or perpendicular to a major surface of), for example, a thin film of CVD diamond by determining the optical absorptivities and the thermal resistivities of the first and second bodies in these directions, respectively.

As known in the mathematical art, if more accuracy is desired in determining the values of A and C, a selection of more than two other bodies can be used and measured for their respective values of $\alpha$ and W, and a best-fitting-straight-line technique can then be used to obtain best values of A and C.

In the case of CVD diamond, in which the main or predominant type of impurity tends to be some sort of carbon, the constants A and C tend to be independent of batches of diamond made in a given CVD chamber under different conditions of such deposition parameters as temperature and pressure, and even independent of the growth technique including microwave plasma, hot filament, or arc jet in a given chamber, as well tend to be independent of the CVD chamber. It is believed that these independences are attributable to the fact that the impurity responsible for the optical absorptivity in all these bodies of CVD diamond is a similar form of some kind of carbon. However, it should be understood that this belief, or any theory for that matter, is not essential for the success of the invention.

In a specific embodiment, this invention involves a method of determing the thermal resistivity $W_s$ of an electrically insulating crystalline or polycrystalline sample (SUT) of host material, containing a concentration of an impurity or of a combination of impurities, comprising the steps of:

measuring the optical absorptivity $\alpha_s$ of the sample (SUT) in a spectral range having wavelengths of significant intensities continuously spanning a range of spectral width approximately equal to at least 200 nm, followed by determining the thermal resistivity $W_s$ of the sample (SUT) by determining the value of $A+C\alpha_s$, where A and C are the constants determined from the equation $W=A+C\alpha$, the values of C and A being determined by measuring the respective thermal resistivities $W_1$ and $W_2$ and by measuring the respective optical absorptivities $\alpha_1$ and $\alpha_2$ of at least first and second bodies comprising the same host material as that of the sample and the same impurity or combination of impurities as that of the sample, but the first and second bodies containing a different concentration of the impurity, or of the combination of impurities, from each other.

Although in the case of anisotropic host materials, the constants A and C can depend upon the direction of propagation of optical radiation and the direction of heat flow through the bodies, the constants A and C are independent of the concentration of the given type of impurities or the combination of the given types of impurities in the given ratio in that material. However, when making measurements of $\alpha$ and W, the same direction of propagation of optical radiation need not be used for measuring $\alpha$ as the direction of heat flow for measuring W; nevertheless, the direction of heat flow with respect to a major plane of the host materials advantageously is the same for the first and second bodies as for the SUTs.

Advantageously, in the cases in which the host material contains a combination of impurities, both in the first and second bodies these impurities have the same weight or molecular ratios among each other as in the SUT.

Advantageously also, the optical absorptivity $\alpha$ of each of the bodies, including the optical absorptivity $\alpha_s$ of the SUT, is measured by measuring the thickness of each of the bodies (such as by known techniques) and by directing a beam of optical radiation of the first (advantageously equal to the second) spectral range R on each of the bodies, followed by measuring the ratio of the optical intensity $I_0$ of the optical radiation directed on the respective body to the optical intensity I of the optical radiation emerging from the respective sample, in order to determine the optical absorptivity of the SUT via equation (3) above. Here the range R refers not only to the upper and lower limits of the spectral range but also to the spectral intensity distribution within the entire range R.

Useful apparatus for performing these measurements and determinations of the optical absorptivities of the first and second bodies and of the SUT using the equation (2) above is disclosed in our patent applications Graebner-Jin 11-110 and Graebner-Jin 12-111 filed simultaneously herewith and hereby incorporated herein.

The constants A and C can also be determined by trial and error: that is to say, trial values of these constants A and C can be selected as a trial set: for a multiplicty of SUTs trial values of $W_{st}=A+C\alpha_s$ can then be calculated using measured values of $\alpha_s$; these trial values of $W_{st}$ can then be compared with measured values of $W_s$ using some other technique of measuring $W_s$ such as is taught in the aforementioned U.S. Pat. No. 5,297,868; and then a new trial set of constants A and C can be selected.

BRIEF DESCRIPTION OF THE DRAWINGS

Only for the sake of clarity, FIG. 1 is not drawn to any scale.

DETAILED DESCRIPTION

EXAMPLE 1: CVD DIAMONDS

Figure 1:
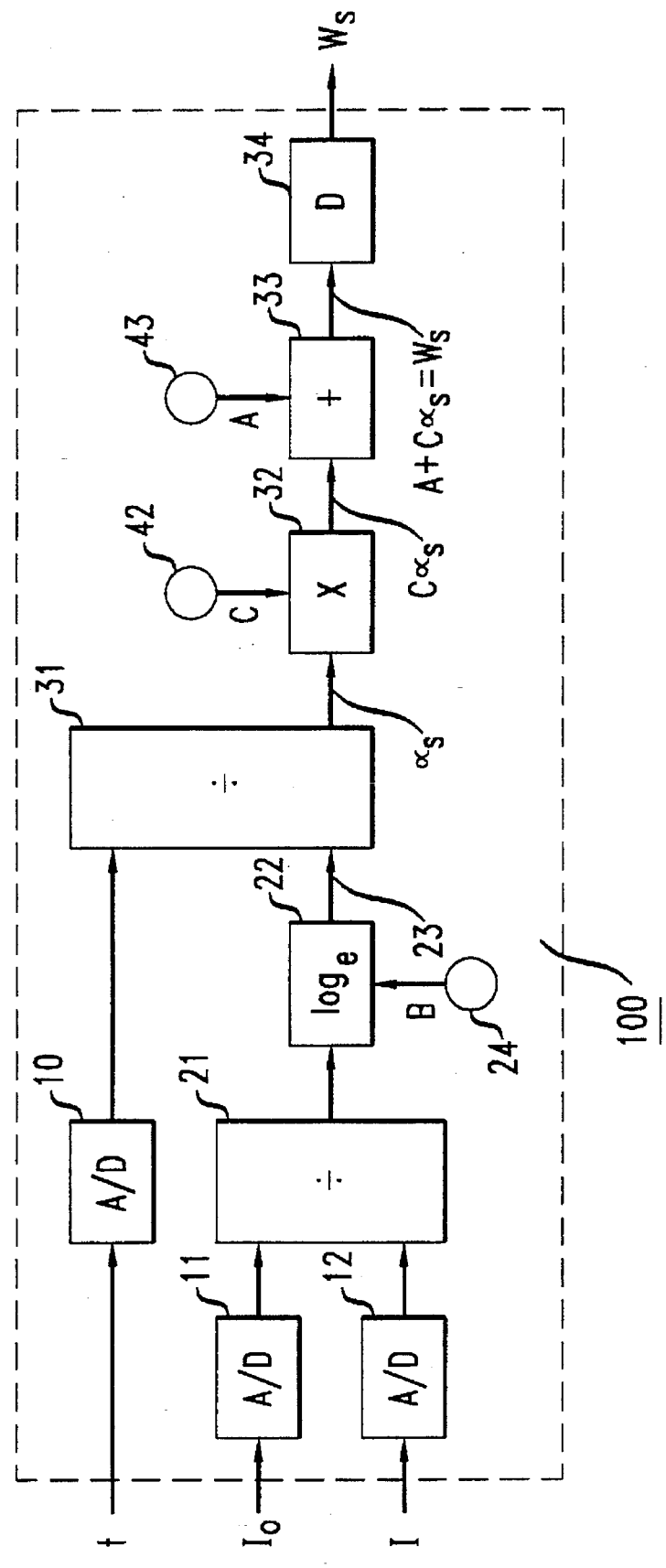
FIG. 1 is a diagram of apparatus useful for performing the steps of this invention.

At least two bodies of CVD diamond films are fabricated, each of the bodies having a major surface, and each of them having been made in the same or different CVD chambers under conditions that result in at least two of them having two different thermal conductivities $W_1$ and $W_2$, respectively, and hence having at least two different optical absorptivities $\alpha_1$ and $\alpha_2$, respectively. Their respective thermal conductivities $W$ in the direction parallel to their major surfaces are respectively measured, for example, by the technique described in the aforementioned U.S. Pat. No. 5,297,868. Using sunlight or artificial source of visible light (the wavelengths $\lambda$, having significant intensities continuously spanning the approximate range of 400 nm–800 nm) as the source of optical radiation propagating through these bodies in the direction perpendicular to their major surfaces, their respective optical absorptivities $\alpha$ in this direction are respectively determined, for example, using equation (3) above.

Advantageously, the values of the optical absorptivities of the two (or more) bodies range over at least one, and preferably three, powers of ten. Then, in the case where $W$ and $\alpha$ of two and only two bodies are used for these determinations of optical absorptivities, a straight line is drawn in a Cartesian graphical plot, either by hand or by machine, between the two resulting points of $W$ vs. $\alpha$, whereby $C$ and $A$ can be determined: the slope of the straight line yields the value of $C$, and the intercept of the straight line with the ordinate (i.e., the point at which $\alpha=0$) in the Cartesian graphical plot yields the value of $A$. More specifically, if $W_1$ and $W_2$ denote the respective measured values of the thermal resistivities of the two bodies, and if $\alpha_1$ and $\alpha_2$ denote the respective measured values of the optical absorptivities of the two bodies, then it follows mathematically that $$C=(W_2-W_1)/(\alpha_2-\alpha_1), \text{ and } A=(\alpha_2 W_1-\alpha_1 W_2)/(\alpha_2-\alpha_1).$$

In the case where the values of $W$ and $\alpha$ of more than two bodies are measured, well-known techniques of straight-line fitting—either human eye, human calculation (using, for example, least squares), or preferably computer machine—can be used to find a best-fitting straight line to fit the equation (2) above, whereby the values of $C$ and $A$ are determined from the slope and intercept of the best-fitting straight line.

Alternatively, having determined the value of the constant $A$ as above, the value of the constant $C$ can be determined as follows. The measured points $(W-A)/A$ vs. $\alpha/\alpha_0$ are plotted on log-log paper, where $\alpha_0$ is a conveniently or arbitrarily selected constant, and where the base of the logarithm is immaterial—the points advantageously spanning at least one power of ten and preferably at least three powers of ten. That is to say, points corresponding to the logarithm of $(W-A)/A$ (to any base of logarithms) are graphically plotted as ordinates (i.e., along the y axis) against the logarithm of $\alpha/\alpha_0$ (to the same base) as abscissae (i.e. along the x axis)—the values of $\alpha/\alpha_0$ spanning at least one power of ten and preferably spanning at least three powers of ten. These points are fitted to a best-fitting straight line having a slope equal to unity, either by means of human eye or by means of well-known mathematical techniques (such as least squares) by human calculation or preferably by computer machine. The value of the constant $C$ can then be determined from the ordinate of the intercept $y=y_0$ on the x axis of the resulting straight line log-log plot; i.e., the value of $y=y_0$ at which $x=0$—i.e., the value of y at which log $(\alpha/\alpha_0)=0$—by means of the equation $$C=(A/\alpha_0) \text{ antilog } (y_0) \qquad (4)$$

as can be derived from equation (2) above.

As a source of optical radiation for measuring the optical absorptivities $\alpha$, instead of, or preferably in addition to a source of visible light, a source(s) of near infra-red optical radiation can be used. Advantageously, in any event the optical source should have wavelengths of significant intensities continuously spanning a range of spectral width approximately equal to at least 200 nm.

The values of $C$ and $A$ having thus been determined in any case, the thermal resistivity $W_s$ of the SUT(s) can be determined merely by measuring the value(s) of the optical absorptivity of the SUT(s) advantageously using the same optical source as was used for measuring the optical absorptivities of the two (or more) bodies, its value being determined by using equation (2).

As a source of optical radiation for measuring the optical absorptivities $\alpha$, instead of, or preferably in addition to a source of visible light, a source(s) of near infra-red optical radiation can be used. Advantageously, in any event the optical source should have wavelengths of significant intensities continuously spanning a range of spectral width approximately equal to at least 200 nm.

As an alternative to the above described method of determining the value(s) of thermal resistivity $W_s$ of the SUT(s), an apparatus 100 of the kind shown in FIG. 1 can be used. As indicated in FIG. 1, the apparatus 100 includes three analog-to-digital converters (hereinafter "A/D converters") 10, 11 and 12. An input t representative of the thickness of the SUT is fed into and received by the A/D converter 10. An input $I_0$ representative of optical radiation directed on the SUT is fed into and received by the A/D converter 11, and an input I representative of the optical radiation emerging from the SUT is fed into and received by the A/D converter 12. These inputs $I_0$ and I can be obtained by conventional methods such as describe in, for example, *Optics Guide* 5, at pages 22–9 through 22–38 (1990), published by Melles Griot, Irvine, Calif. 92714, or by methods that are described in our aforementioned patent applications Graebner-Jin 11-110 and Graebner-Jin 12-111 filed simultaneously herewith and hereby incorporated herein.

The outputs of the A/D converters 11 and 12 are fed into and received by a divider 21. An output $I_0/I$ emerging from the divider 21 thus is a representative of the ratio of the input-to-output intensity $I_0/I$ of the optical radiation directed on and emerging from the SUT. This ratio $I_0/I$ is fed into and received by a natural logarithm converter 22. The natural logarithm converter 22 also receives an input $\beta$ from a source 24—the same $\beta$ as appears in equation (3) above, the value of $\beta$ having been determined by known methods, and having been stored in the source 24—whereby the natural logarithm converter 22 multiplies its input $I_0/I$ by this factor $\beta$, in order to take into account both external optical reflections and multiple internal reflections in the SUTs as discussed above in connection with equation (3). For the case of CVD diamonds as the host material, the value of $\beta$ is approximately equal to 0.71. Thus the output 23 of the natural logarithm converter 22 is a representative of $\log_e (\beta I_0/I)\alpha_s t$, according to equation (3) above. The outputs of the A/D converter 10 and of the natural logarithm converter 22 are received by another divider 31, whereby the output of this divider 31 is a representative of $\alpha_s$, the optical absorptivity of the SUT. Then the output $\alpha_s$ of the divider 31 is received by a multiplier 32 which multiplies the value of $\alpha_s$ by a value of the constant $C$ previously stored in a memory 42, the value of $C$ having been previously determined experimentally using at least the first and second bodies, as described above. The output $C\alpha_s$ of the multiplier 32 is fed into and received by an adder 33 that adds to this value of $C\alpha_s$ the value of the constant $A$ previously stored in a memory 43, the value of $A$ having been previously determined experimentally using at least the first and second bodies, as described above. The output of the adder 33 is thus equal to $A+C\alpha_s$, which is equal to the thermal resistivity $W_s$ of the SUT, as follows from equation (2) above. This output $A+C\alpha_s$ can then be fed into and received by a detector 34 (or sensor or display device), whose output will thus be equal to the desired value of $W_s$. The detector 34 can include amplifier circuitry for the purpose of calibration against known SUTs and for other circuitry purposes as known in the art.

An advantageous alternative to purely visible light, the optical radiation contains significant wavelengths spanning the approximate spectral range anywhere between 10 nm–10,000 nm, the source preferably having wavelengths of significant intensities spanning continuously a range of spectral width approximately equal to at least 200 nm. Still another advantageous alternative source of optical radiation is a source of infra-red radiation (which preferably is combined with visible light) spanning the approximate spectral range of anywhere between 800 nm–10,000 nm, preferably having wavelengths of significant intensities spanning continuously a range of spectral width approximately equal to at least 200 nm.

Instead of measuring the optical absorptivites $\alpha$ and thermal resistivities W of the CVD diamond films and of measuring the optical absorptivity of the SUT in the direction parallel to the major surface of the respective films, these quantities can be measured, and especially W should be measured, in a direction perpendicular to the major surface of the bodies, whereby the thermal resistivity of the SUT in this direction can be determined.

EXAMPLE 2: NATURAL DIAMONDS

Provided that the natural diamonds are sufficiently pure, equation (2) above still holds with the same C and A for all those diamonds having the same single impurity or having impurities in the same proportion among one another. More specifically, in the cases of naturally occurring diamonds: for a given impurity—such as boron (blue diamond) or nitrogen (yellow diamond)—the values of A and C in a given crystalline direction are all the same from diamond body to diamond body provided, for example, that they all contain one and the same type of impurity or a combination of the same types of impurities in a fixed ratio—such as boron, or such as nitrogen, or such as boron and nitrogen in a weight ratio of E/F, where E and F are constants. Typically, diamonds found in the same vein of a diamond mine will satisfy this impurity requirement. More specifically, it is expected that all naturally occurring diamonds originating from the same vein of a mine will contain the same type of impurity but in different impurity concentrations in different locations of the vein. For a body of pure diamond (i.e., containing no significant concentration of any impurities that cause optical absorption), its thermal resistivity W will be equal to $W_0=A+C\alpha_0$, where $W_0$ is the thermal resistivity of the body of pure diamond, and where $\alpha_0$ is the optical absorptivity of the body of pure diamond. Thus, by measuring and determining the C and A for diamonds from a given vein where at different locations of the vein the optical absorptivity is different, the thermal resistivity W can be determined for all other diamonds in this vein simply by measuring their respective optical absorptivity followed by using equation (2) above.

Although the invention has been described in detail in terms of specific embodiments, various modification can be made without departing from the scope of the invention. For example, instead of diamond other crystalline or polycrystalline host materials can be used such as lithium niobate or lithium fluoride containing various impurities, sapphire (typically containing titanium as the impurity), or ruby (typically containing chromium as the impurity).

One of the A/D converters 11 or 12 can be omitted provided the divider 21 is arranged to receive the quantities I and $I_0$ simultaneously or seriatim—in the latter case of which either the remaining A/D converter 11 or 12 or the divider 21 is provided with a temporary memory for storing one of the quantities representative of I or $I_0$. Moreover, the A/D converters 10, 11, and 12 can be omitted provided that the circuit elements—i.e., the adder, the multiplier, the detector, the logarithm converter, and the dividers—can process information, as known in the art. Finally, the logarithm converter 22 need not be a converter to natural logarithms (i.e., to the base e of natural logarithms) but can be a converter to logarithms to other bases, such as to the base ten or to any arbitary base x, provided suitable changes in the mathematics are made—such as dividing the output of the logarithm converter by a factor $\log_e 10$ or $\log_x e$, respectively, in order to obtain the values of the thickness t, or by redefining the value of the constant C in equation (2) above by dividing it by a factor $\log_e 10$ or by a factor of $\log_x 10$, respectively.

What is claimed is:

1. A method of determining the thermal resistivity $W_s$ of an electrically insulating, crystalline or polycrystalline sample (SUT) of host material, containing a concentration of an impurity of a combination of impurities, comprising the steps of:

(a) measuring the optical absorptivity $\alpha_s$ of the sample (SUT) in a spectral range having wavelengths of significant intensities continuously spanning a range of wavelengths having a spectral width approximately equal to at least 200 nm; and (b) determining the thermal resistivity $W_s$ of the sample (SUT) by determining the value of $A+C\alpha_s$, where A and C are the constants determined from the equation $W=[C+A\alpha]A+C\alpha$, the values of C and A being determined by measuring the respective thermal resistivities $W_1$ and $W_2$ by a prior art method, and measuring the respective optical absorptivities $\alpha_1$ and $\alpha_2$ of at least first and second bodies $B_1$ and $B_2$, respectively, comprising the same host material as that of the sample and the same impurity or combination of impurities as that of the sample, but the first and second bodies containing a different concentration of the impurity or of the combination of impurities from each other.

2. The method of claim 1 in which the host material comprises CVD diamond.

3. The method of claim 1 in which the range includes substantially the entire humanly visible range of the optical spectrum.

4. The method of claim 3 in which the host material comprises CVD diamond.

5. The method of claim 1 in which the range includes wavelengths in the visible range of the spectrum.

6. The method of claim 5 in which the host material comprises CVD diamond.

7. The method of claim 1 in which said range of wavelengths includes the approximate range of 10 nm–10,000 nm.

8. The method of claim 7 in which the host material comprises CVD diamond.

9. The method of claim 1 in which the range of wavelengths includes wavelengths in the visible range of the spectrum plus wavelengths outside the visible range of the spectrum having significant intensities in the approximate range of 10 nm–2,000 nm.

10. The method of claim 9 in which the host material comprises CVD diamond.

11. The method of claim 1 in which said range of wavelengths includes the approximate range of 800 nm–2,000 nm.

12. The method of claim 11 in which the host material comprises CVD diamond.

13. The method of claim 1 in which the range of wavelengths includes wavelengths in the visible range of the spectrum plus wavelengths outside the visible range of the spectrum having significant intensities in the approximate range of 800 nm–2,000 nm.

14. The method of claim 13 in which the host material comprises CVD diamond.

15. The method of claim 1 in which said range of wavelengths includes the approximate range of 800 nm–10,000 nm.

16. The method of claim 15 in which the host material comprises CVD diamond.

17. The method of claim 1 in which the range of wavelengths includes wavelengths in the visible range of the spectrum plus wavelengths outside the visible range of the spectrum having significant intensities in the approximate range of 800 nm–1,000 nm.

18. The method of claim 17 in which the host material comprises CVD diamond.

* * * * *